United States Patent [19]

Schweikhardt et al.

[11] Patent Number: 4,925,680

[45] Date of Patent: May 15, 1990

[54] PROCESS FOR ENZYMATIC PRODUCTION OF BIFIDOGENIC INFANT AND DIETETIC FOODS

[75] Inventors: Friedrich Schweikhardt, Friedrichsdorf; Günther Sawatzki, Butzbach; Rainer Braun, Friedrichsdorf, all of Fed. Rep. of Germany

[73] Assignee: Milupa Aktiengesellschaft, Friedrichsdorf, Fed. Rep. of Germany

[21] Appl. No.: 245,756

[22] Filed: Sep. 16, 1988

[30] Foreign Application Priority Data

Jul. 7, 1988 [EP] European Pat. Off. ............ 88110870

[51] Int. Cl.$^5$ ............................ A23C 9/12; A23C 9/13
[52] U.S. Cl. ......................................... 426/42; 426/61; 426/580; 426/585; 426/801; 426/804
[58] Field of Search .................. 426/42, 61, 801, 804, 426/580, 585

[56] References Cited

U.S. PATENT DOCUMENTS 1,935,890 11/1933 Rosenthal ............................ 426/42
3,338,719 8/1967 Sawada et al. ........................ 426/42

FOREIGN PATENT DOCUMENTS 1123647 8/1968 United Kingdom .

*Primary Examiner*—Marianne Cintins
*Attorney, Agent, or Firm*—Scully, Scott, Murphy & Presser

[57] ABSTRACT

The present invention relates to a process for the production of liquid and powdered bifidogenic infant and dietetic foods which are reduced in their antigenicity. The process according to the invention is characterized in that to achieve bifidogenicity, sialic acid is enzymatically cleaved from the milk proteins using the enzyme neuraminidase (sialidase).

Consequently in accordance to the invention it is possible to produce bifidogenic infant foods, particularly suitable for infants, premature and small for date babies, which can additionally be used in cases of intolerances against usual milk products.

Furthermore the process can be used for production of dietetic food, particularly for patients suffering from intestinal allergies, other allergic diseases and patients with insufficiency of liver and kidney.

9 Claims, No Drawings

PROCESS FOR ENZYMATIC PRODUCTION OF BIFIDOGENIC INFANT AND DIETETIC FOODS

The present invention relates to a process for the production of infant and dietetic foods, which are bifidogenic and reduced in antigenicity.

Worldwide mother's milk is considered the optimal nutrition for infants. However, for many reasons mother's milk is not always available for feeding newborns and infants. Since a long time period for that reason milk of mammals, especially cow's milk, has been used for infant foods. Non-modified or fat-reduced cow's milk, i.e. skimmed milk, however is suitable for feeding infants not before the fourth to sixth month. When cow's milk is used as substitute for mother's milk, it is necessary to perform the so-called adaptation. This includes, inter alia, a partial substitution of the milk fat by vegetaable oils. For improving the nutritional value of the protein and for obtaining a higher content of certain essential amino acids, similar to human milk, it is necessary to change the content of cow's milk protein. In principle, for the production of infant foods based on cow's milk it is intended to adapt these products as closely as possible to human milk.

In many publications the production of infant foods based on cow's milk is described. The state of art offers the possibility of obtaining a product considerably corresponding to mother's milk by removing certain parts of the cow's milk and by adding-components similar to mother's milk.

The production of foods with improved protein digestibility and reduced antigenicity has a particular important use for medical purposes beside the application in infant nutrition. This relates to foods particular for patients with intestinal allergies, other allergic diseases (e.g. eczema, urticaria, inter alia), for patients with insufficiency of kidney and liver and for patients with gastro-intestinal disorders.

On the market all infant and dietetic foods based on proteins are characterized by the intact specific antigenicity of the protein component. The enzymatic or acidolytic digestion of dietary proteins leads to a nearly complete loss of the antigenicity, but the oligopeptide or elemental diets produced by this technique result in a drastic deterioration in taste, which causes almost generally a refusal of those foods by the patients. The antigenicity of dietary proteins still leaves an unresolved problem in the adaptation to mother's milk of infant foods based on cow's milk or soy proteins and in the production of easily digestible diets for medical purposes.

All well known infant foods based on cow's milk used as substitute for mother's milk have the disadvantage of being non-bifidogenic. Bifidogenic factors subsume, inter alia, oligosaccharides containing, inter alia, N-acetyl-D-glucosamine, N-acetylgalactosamine, L-fucose, lactose, D-glucose and D-galactose. These are growth factors for *Lactobacillus bifidus* which manifest dominantly in the intestinal flora of breast-fed infants. The absence of bifidogenicity in all known substitutes for mother's milk based on milk of mammals, especially cow's milk, was previously accepted, because no possibility was realized for adding such a bifidogenic factor to human milk substitutes or to develop this in these substitutes. The present invention is therefore based on the consideration that by splitting off sialic acid, the bifidogenic oligosaccharides of the residual protein will be accessible to the bifidus bacteria acting as growth factors.

The invention is assigned to present a process for the production of bifidogenic infant and dietetic foods.

The invention relates to a process for the production of bifidogenic infant and dietetic foods, in which milk, milk components or milk products of mammals are adapted by the known means (adapted to human milk) and characterized in that for obtaining bifidogenicity, sialic acid is cleaved by the enzyme neuraminidase (sialidase) from the milk proteins.

The present invention does not relate to the commonly known adaptation to human milk, of milk, milk components or milk products. This is presumed as generally known. On the contrary, it is the essence of the invention, that sialic acid is cleaved enzymatically from the milk proteins and their digestion products. Sialic acid is also known as N-acetyl neuraminic acid. According to the present invention sialic acid is cleaved from its bond to the residual protein.

With the term milk of mammals in particular cow's milk is implied subsequently. In certain cases milk of other mammals i.e. of goats, sheep or mares may be taken into consideration.

In the intention of the present invention "milk" is used for full-cream milk and skimmed milk; milk components subsume dietary proteins gained or gainable from milk, especially casein, caseinates, whey proteins (also demineralized), milk protein fractions, proteins from skimmed and for full-cream milk as well as milk products e.g. quarg.

In vitro and in vivo investigations surprisingly have shown that the specific antigenicity of cow's milk proteins can be destroyed extensively by digestion with pepsin within 30 to 60 minutes. This process is pH-dependent and is carried out optimally at pH 2, delayed at pH 3, and above pH 4 there is practically no reaction. The digestion with trypsin at pH 8 does not lead to any loss of specific antigenicity. Due to the normal process of digestion in the stomach, it is prevented that antigenic milk proteins can be transported into the intestine, adhere to the mucosa and permeate the mucosal barrier. Increased pH values in the stomach, occuring physiologically in young infants and frequently in allergic diathesis, lead to an increased antigen challenge of the organism caused by foreign proteins and may initiate allergic deseases such as cow's milk protein intolerance.

In the European patent application No. 8810 284.2, having the title "Process for producing bifidogenic infant and dietetic foods reduced in antigenicity", a process is described, in which milk, milk components or milk products from mammals are adapted by the known means and sialic acid is cleaved from the milk proteins and their digestion products for obtaining bifidogenicity. The cleavage in the process, described there, is performed with hydrochloric acid or a mixture of hydrochloric acid and phosphoric acid in a pH range from 1 to 3.

A much more moderate and therefore technically advantageous method for cleaving sialic acid from the milk proteins is the enzymatic method used in accordance with the invention. According to the invention the cleaving of the sialic acid from the milk proteins is performed enzymatically by using neuraminidase (sialidase). Neuraminidase splits off neuraminic acid from glycosides and glycoproteins containing neuraminic acid at the α-O-glycosidic bond between carbohydrate and the N-acetyl neuraminic acid.

The enzymatic cleavage takes place in a pH range from 4.0 to 8.0 and generally in a temperature range from 4° to 40° C., preferably at 15° to 30° C. The optimal pH range is from 5.2 to 6.5, which can optionally be adjusted by means of hydrochloric acid, phosphoric acid, citric acid and other suitable organic acids. The time period required for the enzymatic cleavage is, as usual, dependent on temperature and also depends on the activity of the enzyme respectively used. It amounts to about 10 minutes up to 24 hours.

Neuraminidase (sialidase) can be immobilized in the usual way. Immobilization procedures for immobilizing enzymes are known from the state of art. The conventional immobilization procedures can be used. The advantage in using the immobilized enzyme is to be seen in the fact that the enzyme can be easily separated after the enzymatic reaction by conventional process, such as centrifugation or filtration, and can be recycled. When using the non-immobilized enzyme, the free enzyme can remain in the product. This is particularly the case in a batch process. The enzyme can be inactivated by a short-term heat treatment.

The advantage of the enzymatic cleavage is the moderate treatment of the protein and the improvement in the further processing by dairy technology.

After the hydrolysis, neutralization is performed with phosphates, citrates and other suitable anions, e.g. sodium or calcium phosphates and citrates, because with this process such strong buffering is not required. The mineral content of the complete food is optimized by the addition of the corresponding cations.

After splitting off the sialic acid it is of proper use to heat the product for a short term to a temperature from 80° to 100° C. to reduce further the specific antigenicity of the milk protein. This stage, however, may be a typical process step used in the preparation of infant and dietetic foods based on milk, milk components or milk products (adaptation), e.g. sterilization or paotcurization.

A suitable process for the enzymatic cleavage of the sialic acid from the milk proteins is given below. The process in accordance with the invention can thus be performed by the following stages:

(a) ultra high temperature heating of the milk or milk protein/milk mixture,
(b) buffering of the said mixture by addition of hydrochloric acid, phosphoric acid, citric acid or another suitable organic acid to pH 4.5 to 7.0,
(c) addition of neuraminidase (sialidase) to the milk or the milk product,
(d) keeping the mixture in accordance with (c) for a sufficient time period (10 minutes to 24 hours) at a pH ranging from 4.0 to 8.0 for cleaving the sialic acid from the proteins at a temperature from 4° to 60° C.,
(e) optional heating to 85° to 100° C. for 5 to 15 seconds in order to inactivate the neuraminidase at the end of the hydrolysis in accordance with (d),
(f) neutralization and/or buffering with KOH, $K_2CO_3$ or with phosphates and for citrates of potassium, sodium and calcium,
(g) addition of the typical supplements which are used for adaptation and conventional technical dairy processing of the mixture, and
(h) spray dying of the mixture obtained in accordance with (g).

In the technical implementation of the process it is practical and usual either before or after the single process stages to perform a homogenization of the mixture in suitable homogenizing machines. This is oriented on the respective technical conditions. In principle the process according to the invention can be integrated in the commonly used equipment for the production of infant or dietetic foods based on milk or milk products without large additional investment.

The process in accordance with the invention makes possible the production of bifidogenic infant and dietetic foods. To establish a bifidogenic effect it is necessary to add lactose and/or other suitable carbohydrates (e.g. maltose). Beside establishing the bifidogenic property, the antigenicity is also reduced. The residual protein acts as lectin inhibitor and therefore is effective as bifidus growth factor, because bifidogenic oligosaccharides become accessible for *Lactobacillus bifidus.*

Infant foods produced with the said process establish a bifidus flora such as an infants fed mother's milk. Due to the development of this bifidus flora in the intestine of the infants, a protection against infection could be established during the first month of life, as it is the case for breast-fed infants. Infant and dietetic foods produced in accordance with the said process have improved digestibility and acceptance.

The invention will be further illustrated in the Examples which follow.

EXAMPLE 1

75 kg demineralized whey powder (78% protein in dry solids) and 42 kg acid casein are dissolved in 1000 l water. The mixture is sterilized at 140° C. for 4 seconds by an ultra-high-temperature heater. Afterwards, the mixture is cooled to 37°–40° C. Then the product is buffered, using hydrochloric acid and/or citric acid to adjust a pH of 5.2 to 6.5.

25000 to 100000 U neuraminidase are added to the mixture. Afterwards, the mixture is incubated for 5 hours at a temperature of 30° C. and at a pH ranging from 4.8 to 6.0. The time of incubation is 3–4 hours.

Using an immobilized neuraminidase (100,000–1,000,000 Units neuraminidase), the enzyme is separated by centrifugation or filtration after the enzymatic reaction. Optionally the separated immobilized enzyme can be used again for a further production. If a nonimmobilized neuraminidase is used, then the enzyme is inactivated by heating the batch to 95°–100° C. for 5–10 seconds. Afterwards, the batch is cooled to 70° C. Then, 560 kg lactose, 200 kg vegetable fat blend, 3 kg emulsifier, 83 kg milk fat, and 3.8 kg potassium chloride are added. Then the mixture is homogenized at 200 bar at 65° C. and transferred into an intermediate tank. Minerals and trace elements are added. Then the batch is again homogenized at 100 bar. The homogenized mixture is pasteurized at 85° C. and spray dried. The obtained powder is mixed with a vitamin mix; subsequently the vitaminized power is packaged or instantized.

This product, manufactured by the described process, is suitable for the nutrition of infants and premature babies, which are sensitive against cow's milk or other breast milk substitutes.

EXAMPLE 2

Production of a dietetic food for patients with gastrointestinal disorders

| Composition | |
| --- | --- |
| acid casein | 33.80 kg |

| Composition | | |
|---|---|---|
| demineralized whey protein (75% protein, dry solids) | 55.90 | kg |
| butter fat | 107.10 | kg |
| corn oil | 164.30 | kg |
| emulsifiers | 6.00 | kg |
| starch | 71.50 | kg |
| lactose | 512.52 | kg |
| vitamin mix | 3.00 | kg |
| mineral mix | 33.25 | kg |
| citric acid | 0.50 | kg |
| calcium carbonate | 4.65 | kg |
| potassium hydroxide | 3.38 | kg |
| sodium hydroxide | 2.87 | kg |
| sodium hydrogen phosphate | 0.73 | kg |
| magnesium hydroxide carbonate | 0.50 | kg |
| | 1000.00 | kg |

Amount of enzyme for the enzymatic hydrolysis: 25000–100000 Units neuraminidase /100 kg powder 55.9 kg demineralized whey protein concentrate (75% protein in dry solids) and 33.8 kg acid casein are dissolved in 1,000 l water. The mixture is sterilized at 140° C. for 4 seconds with an ultra-high-temperature heater. Afterwards, the mixture is cooled to 37°–40° C. and buffered to a pH of 4.5–6.5, using hydrochloric acid and/or citric acid, 25,000–100,000 U neuraminidase are added to the mixture. The mixture is kept for 5 hours at a pH of 4.8–6.0 and at a temperature of 37°–40° C. The time of incubation is 3–4 hours. Using an immobilized neuraminidase ($10^5$–$10^6$ Units neuraminidase), the enzyme is separated by centrifugation or filtration after the enzymatic reaction. Optionally the separated immobilized enzyme can be used again for a further production. If a non immobilized neuraminidase is used, then the enzyme is inactivated by heating the batch to 95°–100° C. for 5–10 seconds. Afterwards the mixture is cooled to 70° C. Then, the other components as fats, emulsifiers, carbohydrates, and mineral substances are added. Afterwards, the mixture is homogenised at 200 bar at a temperature of 65° C. and transferred to an intermediate tank. Vitamins are added and stirred for 10 minutes. Then the mixture is pasteurized at a temperature of 85°–90° C. The mixture is spray dried as usual. The obtained powder is packaged or instantized before packaging.

The product is suitable as a dietetic food for patients with gastrointestinal disorders.

| Analysis: | | |
|---|---|---|
| 100 ml ready to feed formula contain: | | |
| protein | 1.0 | g/100 ml |
| carbohydrates | 8.5 | g/100 ml |
| lactose | 7.5 | g/100 ml |
| starch | 1.0 | g/100 ml |
| fat | 3.8 | g/100 ml |
| butter fat | 1.5 | g/100 ml |
| vegetable fat | 2.3 | g/100 ml |
| minerals | 0.2 | g/100 ml |
| Na | 28 | mg/100 ml |
| K | 48 | mg/100 ml |
| Ca | 34 | mg/100 ml |
| Mg | 3 | mg/100 ml |
| P | 14 | mg/100 ml |

We claim:

1. A process for producing bifidogenic infant and dietetic foods from mammalian milk material containing a mixture of milk protein and milk protein degradation products, said milk material being selected from the group consisting of mammalian milk, mammalian milk components, and mammalian milk products which comprises adding sufficient neuraminidase enzyme to said milk material to cleave sialic acid from said milk protein and adding sufficient carbohydrate to obtain bifidogenicity.

2. A process as claimed in claim 1 wherein an immobilized neuraminidase is used.

3. A process according to claims 1 or 2 wherein the carbohydrate is lactose or maltose.

4. A process as in claim 1 or 2, comprising the following steps:
   (a) heating the mammalian milk or mammalian milk protein to an ultra-high temperature,
   (b) adjusting the pH of the mixture to 4.5–7.0,
   (c) adding a sufficient amount of neuraminidase to the mixture to cleave sialic acid therefrom,
   (d) incubating the mixture in accordance with (c) for a sufficient period, at a sufficient temperature, and a sufficient pH to cleave the sialic acid from the mixture,
   (e) adding to the mixture, a sufficient amount of base to neutralize the mixture;
   (f) adding dairy supplements selected from the group consisting of fats, emulsifiers, carbohydrates, minerals and trace elements,
   (g) pasteurizing the mixture; and
   (h) spray-drying the resulting mixture.

5. The process of claim 4 wherein the step (b), the acid used to adjust the pH is selected from the group consisting of hydrochloric acid, phosphoric acid and citric acid.

6. The process of claim 4 wherein in step (e) the mixture is incubated for 10 minutes to 24 hours at 4°–60° C. and at a pH of 4.0–8.0.

7. The process of claim 4 wherein in step (f) the base used to neutralize the mixture is KOH, $K_2CO_3$ or phosphates and citrates of potassium, sodium and calcium.

8. The process of claim 4 which further comprises heating the mixture at the conclusion of incubation to a temperature sufficient to inactivate the neuraminidase.

9. The process according to claim 8 wherein the mixture is heated from about 85° C. to about 100° C. for about 5–15 seconds.

* * * * *